United States Patent
Kim et al.

(10) Patent No.: US 7,280,694 B2
(45) Date of Patent: Oct. 9, 2007

(54) APPARATUS AND METHOD FOR IDENTIFYING AN ORGAN FROM AN INPUT ULTRASOUND IMAGE SIGNAL

(75) Inventors: Nam Chul Kim, Daegu (KR); Su Jin Park, Daegu (KR); Young Seuk Song, Seoul (KR)

(73) Assignee: Medison Co., Ltd., Hongchun-gun (KR)

( * ) Notice: Subject to any disclaimer, the term of this patent is extended or adjusted under 35 U.S.C. 154(b) by 998 days.

(21) Appl. No.: 10/617,027

(22) Filed: Jul. 11, 2003

(65) Prior Publication Data
US 2004/0019276 A1 Jan. 29, 2004

(30) Foreign Application Priority Data
Jul. 23, 2002 (KR) .................. 10-2002-0043132

(51) Int. Cl.
*G06K 9/00* (2006.01)
(52) U.S. Cl. .................. 382/181; 382/128; 382/280; 600/437; 600/443; 600/463; 128/916
(58) Field of Classification Search .......... 382/181, 382/190, 100, 191, 207, 214, 106, 107, 128, 382/130–134, 254, 255, 263, 264, 276, 280, 382/277; 600/463, 462, 437, 461, 448, 455, 600/459, 467, 458, 443, 444, 445, 446, 447; 128/916, 925, 915; 73/642; 424/9.52, 9.5, 424/602, 9.42, 9.51, 600; 977/904, 929
See application file for complete search history.

(56) References Cited

U.S. PATENT DOCUMENTS

| | | | | |
|---|---|---|---|---|
| 5,454,371 A * | 10/1995 | Fenster et al. | ............... | 600/443 |
| 6,106,466 A * | 8/2000 | Sheehan et al. | ............ | 600/443 |
| 6,334,847 B1 * | 1/2002 | Fenster et al. | ............... | 600/443 |
| 6,366,687 B1 * | 4/2002 | Aloni et al. | ................. | 382/144 |
| 6,444,192 B1 * | 9/2002 | Mattrey | ...................... | 424/9.52 |
| 6,461,298 B1 * | 10/2002 | Fenster et al. | ............... | 600/437 |
| 6,549,646 B1 * | 4/2003 | Yeh et al. | .................... | 382/132 |
| 7,123,762 B2 * | 10/2006 | Giger et al. | ................ | 382/132 |

FOREIGN PATENT DOCUMENTS

| | | |
|---|---|---|
| JP | 60-171570 | 9/1985 |
| JP | 9-84793 | 3/1997 |
| JP | 2001-161686 | 6/2001 |
| JP | 2002-109510 | 4/2002 |
| WO | WO 00/26852 | 5/2000 |

* cited by examiner

*Primary Examiner*—Sheela Chawan
(74) *Attorney, Agent, or Firm*—Oblon, Spivak, McClelland, Maier & Neustadt, P.C.

(57) ABSTRACT

This invention discloses an apparatus and method for identifying an organ within a human body by calculating the distances of an input ultrasound image signal and the ultrasound image signals classified by the predetermined types of organs in a database, which is based on the feature vectors of the inputted ultrasound image signal and the average vector and the standard deviation vector of the ultrasound image signals, thereby determining an ultrasound image signal having the shortest distance among the calculated distances as the optimal organ image signal for the input ultrasound image signal.

16 Claims, 5 Drawing Sheets

US 7,280,694 B2

APPARATUS AND METHOD FOR IDENTIFYING AN ORGAN FROM AN INPUT ULTRASOUND IMAGE SIGNAL

FIELD OF THE INVENTION

The present invention relates to an ultrasound diagnostic system, and more particularly, to an organ identifying apparatus used in an ultrasound diagnostic system and a method for identifying internal organs from an ultrasound image signal.

BACKGROUND OF THE INVENTION

An ultrasound diagnostic imaging system is a piece of medical equipment that enables the internal organs of a human body to be diagnosed without having to perform invasive or surgical operations upon the human body. In an ultrasound diagnostic imaging system, ultrasound waves are transmitted to a diagnostic area of the human body, ultrasound waves reflected from an internal organ are detected and the reflected ultrasound waves are processed to create and display an image of the organ.

After capturing the displayed image of the organ, the radiologist must analyze the displayed image to make sure that the image is the one for the organ of interest. The radiologist then sets various image parameters, such as depth, contrast, focusing adjustment, gain, degree of edge enhancement, and frame averages, of the ultrasound image signals to an appropriate value for each diagnostic area in order to obtain a clear image of the organ. Therefore, every time the ultrasound diagnostic system is applied to a different area of the human body, the radiologist must identify the organ to be imaged and manually set image parameters according to the target organ.

Accordingly, there exists a need in the art to provide an apparatus and method for automatically identifying the organ to be imaged or displayed.

SUMMARY OF THE INVENTION

Therefore, an objective of the present invention is to provide an apparatus and method for automatically identifying internal organs of a human body from the input ultrasound image signal.

In accordance with one aspect of the present invention, there is provided an apparatus for identifying human organs from an input ultrasound image signal, comprising: a first feature vector determiner for determining a first feature vector of the input ultrasound image signal; a memory for storing a list of predetermined types of organs and a plurality of ultrasound images in association with each of the predetermined types of organs; a second feature vector determiner for determining respective second feature vectors of the ultrasound images for each of the predetermined types of organs; a calculator for calculating an average vector and a standard deviation vector of the second feature vectors for each of the predetermined types of organs; and an organ determiner for selecting one of the average vectors for the predetermined types of organs based on the first feature vector and the average vectors and the standard deviation vectors for the predetermined types of organs, and determining an organ corresponding to the selected average vector as an organ corresponding to the input ultrasound image signal.

In accordance with another aspect of the present invention, there is provided a method for identifying human organs from an input ultrasound image signal comprising the steps of: determining a first feature vector of the input ultrasound image signal; storing in a memory a list of predetermined types of organs and a plurality of ultrasound images in association with each of the predetermined types of organs; determining respective second feature vectors of the ultrasound images for each of the predetermined types of organs; calculating an average vector and a standard deviation vector of the second feature vectors for each of the predetermined types of organs; selecting one of the average vectors based on the first feature vector and the average vectors and the standard deviation vectors for the predetermined types of organs; and determining an organ corresponding to the selected average vector as an organ corresponding to the input ultrasound image signal.

BRIEF DESCRIPTION OF DRAWINGS

The above and other objects and features of the present invention will become apparent from the following description of the embodiments given in conjunction with the accompanying drawings.

DETAILED DESCRIPTION OF THE PRESENT INVENTION

Figure 1:
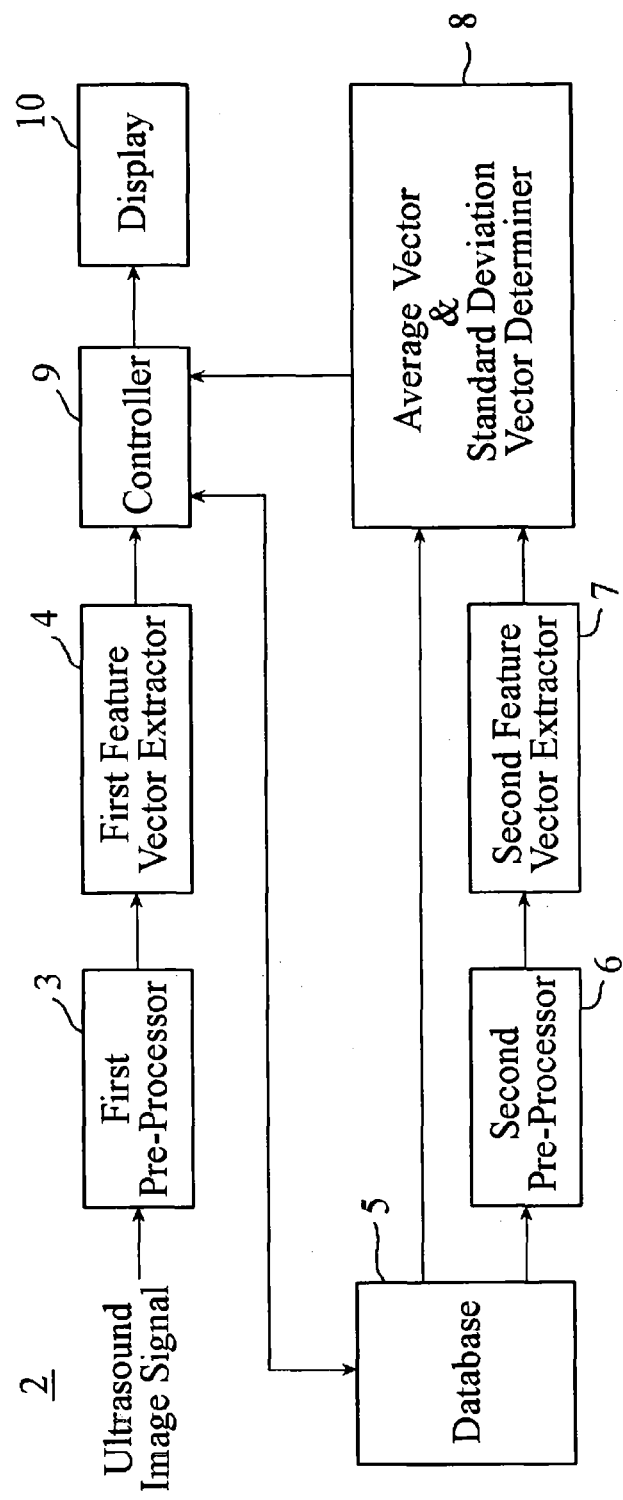
FIG. 1 shows a block diagram of an apparatus for recognizing organs from ultrasound image signals in accordance with an embodiment of the present invention.

Referring to FIG. 1, apparatus 2 generally includes first pre-processor 3, first feature vector extractor 4, controller 9, display 10, database 5, second pre-processor 6, second feature vector extractor 7, and average vector and standard deviation vector determiner 8. First pre-processor 3 receives an ultrasound image signal obtained from a probe (not shown) of the ultrasound diagnostic imaging system and removes noises therefrom. In addition, first pre-processor 3 pre-processes the noise-removed ultrasound image signal in order to prepare for the subsequent signal processing. The functions of first pre-processor 3 will be explained in more detail below with reference to FIG. 2.

Figure 2:
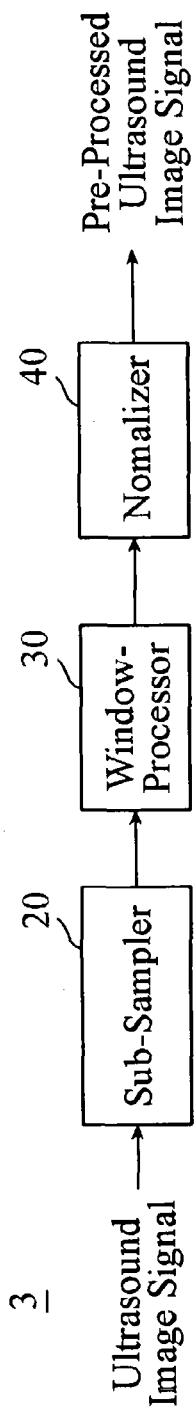
FIG. 2 shows a detailed block diagram for illustrating a first pre-processor shown in FIG. 1.
Figure 3A:
FIG. 3A illustrates an ultrasound image outputted from a probe of an ultrasound diagnostic imaging system.
Figure 3B:
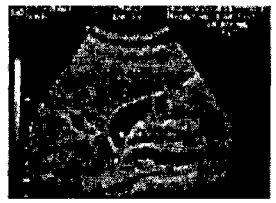
FIG. 3B illustrates an ultrasound image resulting from sub-sampling at a rate of $(4:1)^2$ of an ultrasound image shown in FIG. 3A in accordance with the present invention.

Referring to FIG. 2, first pre-processor 3 includes sub-sampler 20, window processor 30, and normalizer 40. Sub-sampler 20 sub-samples the ultrasound image signal to reduce the size of the ultrasound image signal, thereby enhancing the overall processing speed. In order to minimize loss or distortion arising from sampling the ultrasound image signal, subsampler 20 may preferably sub-sample the ultrasound image signal at the ratio of $(4:1)^2$. For purposes of illustrating the subsampling process, an original ultrasound image as outputted from a probe of the ultrasound diagnostic imaging system, and an ultrasound image as sub-sampled at a ratio of $(4:1)^2$ are shown in FIGS. 3A and 3B, respectively.

Figure 4:
FIG. 4 illustrates an ultrasound image resulting from window-processing of an ultrasound image shown in FIG. 3B.

Window processor 30 performs a windowing process with respect to the subsampled ultrasound image signal so that unnecessary components contained in the ultrasound image signal, which may have an undesirable influence on the extraction of feature vectors at first feature vector extractor 4, are removed. In other words, the image of FIG. 3B includes a text region (in the upper section) bearing information relating to date, patient, diagnostic region and depth, as well as a region for indicating information on brightness and focus (left section). Since this information may hamper the extraction process of feature vectors of an organ, window processor 30 performs a conventional windowing process with respect to the subsampled ultrasound image signal. FIG. 4 illustrates an ultrasound image resulting from window-processing the ultrasound image of FIG. 3B.

Figure 5:
FIG. 5 illustrates a normalized ultrasound image resulting from normalizing an ultrasound image shown in FIG. 4.

The windowing-processed ultrasound image signal is provided to normalizer 40. Normalizer 40 normalizes the brightness and contrast of the windowing-processed ultrasound image signal. Generally, ultrasound image signals obtained from the ultrasound diagnostic imaging system naturally have different brightness and contrast values from each other. These non-uniform values of brightness and contrast may have an undesirable influence on obtaining a spectrum of the ultrasound image signal at first feature vector extractor 4. Therefore, normalizer 40 normalizes the windowing-processed ultrasound image signal in order to provide fixed values of brightness and contrast. The normalization is performed according to Equation 1 by using brightness $\mu$ and standard deviation $\sigma$ of the windowing-processed ultrasound image signal, and average brightness $\mu_d$ and average standard deviation $\sigma_d$ of the ultrasound image signals for a particular organ of interest that are stored in database 5:

$$I_N(m,n) = \mu_d + \frac{(I(m,n) - \mu)}{\sigma} \times \sigma_d \qquad \text{Eq. 1}$$

where (m,n) represents the coordinate position of an organ in the ultrasound image, $I_N(m,n)$ represents the normalized ultrasound image, and I(m,n) represents the windowing-processed ultrasound image. FIG. 5 illustrates a normalized ultrasound image resulting from normalizing the ultrasound image of FIG. 4.

Figure 6:
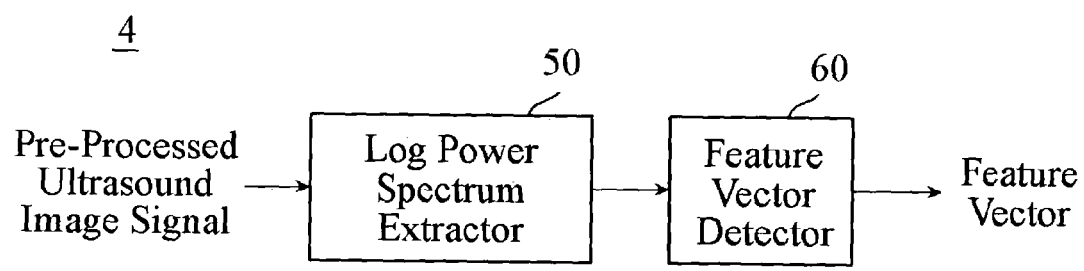
FIG. 6 is a detailed block diagram of a first feature vector extractor shown in FIG. 1.

Referring back to FIG. 1, first feature vector extractor 4 extracts feature vectors from the pre-processed ultrasound image signal. As shown in FIG. 6, first feature vector extractor 4 includes log power spectrum extractor 50 and feature vector detector 60.

Logarithmic power spectrum extractor 50 extracts the log power spectrum of the pre-processed ultrasound image signal. The extracted log power spectrum can be factored into the components corresponding to the scanning ultrasound pulses and the components corresponding to ultrasound waves reflected from the organ tissues. This characteristic of the log power spectrum allows the removal of the components corresponding to the scanning ultrasound pulses, which hampers the recognition of the organs, and thus, the effective detection of the frequency components (response components) corresponding to the low and intermediate frequency bands of the ultrasound waves reflected from the organ tissues. In this way, the adverse effect of noise in the ultrasound image signals and the constant motion of the organ with time can be addressed effectively, which facilitates the determination of the feature unique to the organ.

Figure 7:
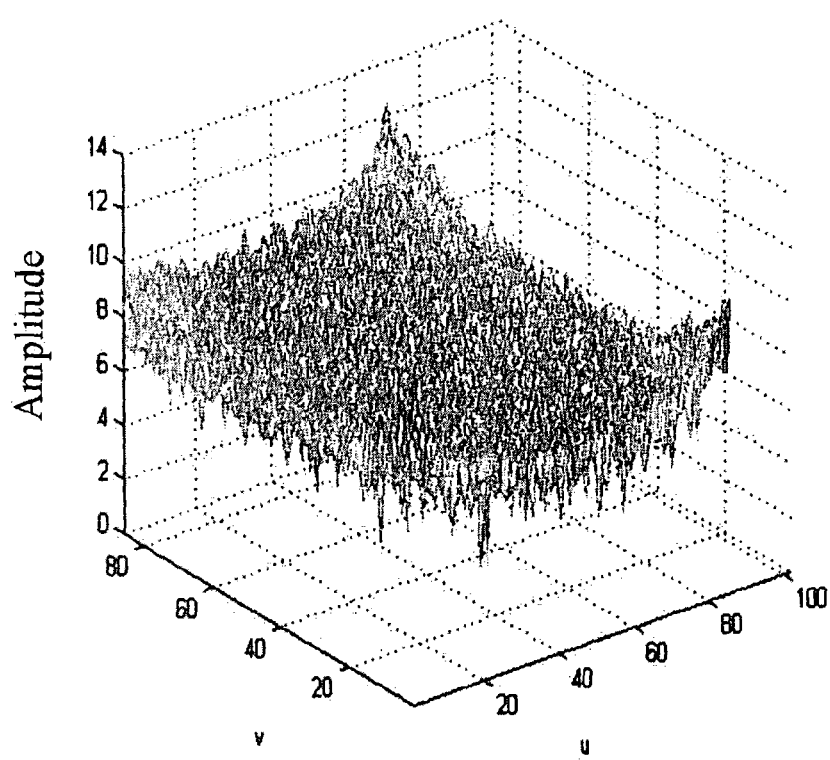
FIG. 7 illustrates a log power spectrum of an ultrasound image signal shown in FIG. 5.

The log power spectrum F(u,v) of the pre-processed ultrasound image signal can be obtained from Equation 2:

$$F(u,v) = \log|\Im\{I_N(m,n)\}| \qquad \text{Eq. 2}$$

where (m,n) is a coordinate position of an organ in the ultrasound image, $I_N(m,n)$ is the normalized ultrasound image signal, $\Im$ is a Discrete Fourier Transform operator, and u are v are frequency variables of the log power spectrum. As can be seen from Equation 2, the log power spectrum of the pre-processed ultrasound image signal is computed using the Discrete Fourier Transform. The symmetry of the Discrete Fourier Transform in the frequency region allows the reduction of the dimensions of the feature vectors required for the recognition of the organs, which results in the reduction of time required for recognition of the organs. The dimension of the feature vectors means the number of components of the feature vectors, and the computation between the feature vectors decreases as the components of the feature vectors decrease. FIG. 7 illustrates the log power spectrum extracted by log power spectrum extractor 50 from the pre-processed ultrasound image signal.

Feature vector detector 60 detects the components, which are required for recognizing organs, of the low and intermediate frequency bands from the log power spectrum and determines them as the feature vectors of organs. The feature vectors of the organs allow mathematical analysis of the components having the most representative characteristics of the organs. The feature vectors of organs in an embodiment of the present invention mean the components of the low and intermediate frequency bands detected from the log power spectrum. The feature vector f of an organ is determined from Equation 3:

$$f = \{F(0.0), F(0.1), \ldots, F(U,V)\} \qquad \text{Eq. 3}$$

where U and V are integers for delimiting a predetermined frequency region to determine the feature vector f of the organ.

Figure 8A:
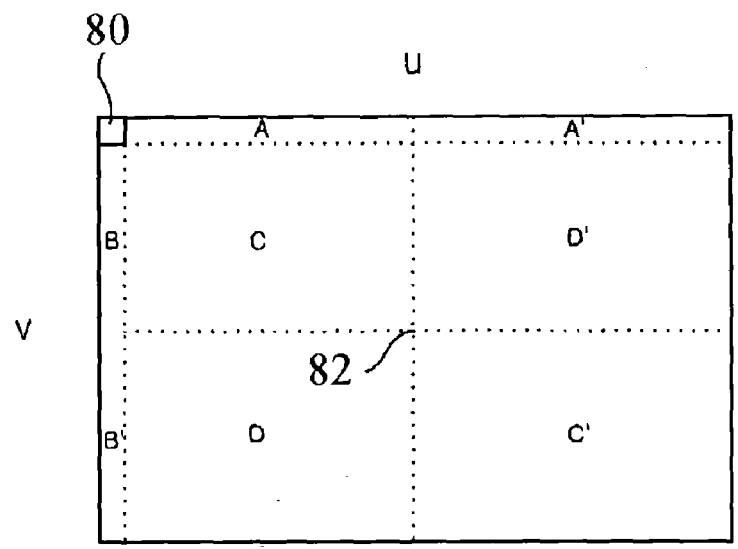
FIG. 8A illustrates a distribution of frequency components of an ultrasound image signal, as pre-processed in accordance with the present invention, in a Discrete Fourier Transform (DFT) domain.
Figure 8B:
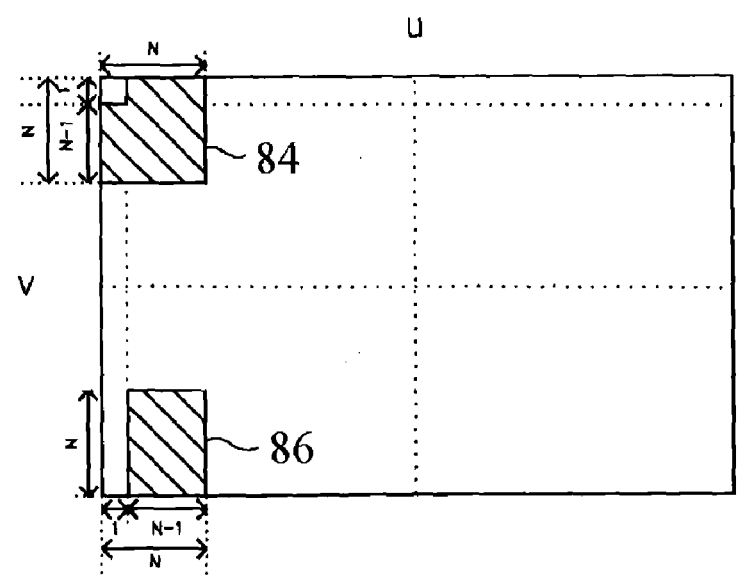
FIG. 8B illustrates a way of selecting necessary frequency components within low and intermediate frequency bands from frequency components shown in FIG. 8A.

Referring to FIGS. 8A and 8B, a detailed description follows of detecting the components of the low and intermediate frequency bands required for recognizing an organ from the log power spectrum.

The frequency bands shown in FIG. 8A include the real and imaginary components of the Discrete Fourier Transform of the pre-processed ultrasound image signal. The real components correspond to regions A and A' and B and B' due to the even symmetry of the Discrete Fourier Transform, and the imaginary components correspond to C and C' and D and D' due to the odd symmetry of the Discrete Fourier Transform. Only A, B, C and D regions or A', B', C' and D' regions are used to extract the feature vectors of an organ in order to reduce the dimensions of the feature vectors. Square region 80 in the upper left corner of FIG. 8A is a DC component of the pre-processed ultrasound image signal and represents the average brightness of the inputted ultrasound image signal. The frequency level becomes higher as it passes through intersection 82 in the diagonal direction of square region 80. Since signals in the low and intermediate frequency bands are generally much stronger than noise, a large signal to noise ratio ("SNR") is maintained. However, the SNR becomes lower as the frequency level becomes higher, where the noise interfere the recognition of an organ.

Accordingly, as shown in FIG. 8B, feature vector detector 60 of a preferred embodiment of the present invention detects the components of the low and intermediate frequency bands having a relatively high SNR and N means the number of feature vectors selected on U and V axes. For example, feature vector detector 60 detects the components of upper left region 84 corresponding to the low frequency bands other than the region of the DC component of the pre-processed ultrasound image signal. However, in the intermediate frequency bands, feature vector detector 60 detects only the components of lower left region 86 other than the frequency components corresponding to the region of B' shown in FIG. 8A, because of the symmetry of the Discrete Fourier Transform. The feature vectors extracted from the log power spectrum of the ultrasound image signals are provided to controller 9 as shown in FIG. 1.

Referring back to FIG. 1, database 5 stores the ultrasound image signals classified by the predetermined types of organs. Further, classification information representing the names of the predetermined organs is also stored in database 5.

Second pre-processor 6 and second feature vector extractor 7 perform the same pre-processing and feature vector extraction for the ultrasound image signals in database 5 as first pre-processor 3 and first feature vector extractor 4. A detailed description of second pre-processor 6 and second feature vector extractor 7 is omitted.

Average vector and standard deviation vector determiner 8 determine the average vector and the standard deviation vector for the ultrasound image signals classified by the types of organs using the feature vectors extracted by second feature vector extractor 7 from the ultrasound image signals classified by the types of organs and the classification information from database 5. The average vector $\overline{F}_k(u,v)$ for ultrasound image signals of the k-th organ can be expressed as in Equation 4:

$$\overline{F}_k(u, v) = \frac{1}{M} \sum_{i=1}^{M} F_k^i(u, v), k = 1, 2, \ldots, K \qquad \text{Eq. 4}$$

where $F^i_k(u,v)$ is the feature vector of the i-th ultrasound image signal for the k-th organ, and M is the number of the ultrasound images for the k-th organ in database 5. The standard deviation vector $\sigma_k(u,v)$ for the ultrasound images for the k-th organ can be expressed as in Equation 5:

$$\sigma_k(u, v) = \left\{ \frac{1}{M} \sum_{i=1}^{M} \{F_k^i(u, v) - \overline{F}_k(u, v)\}^2 \right\}^{\frac{1}{2}} \quad k = 1, 2, \ldots, K \qquad \text{Eq. 5}$$

Figure 9:
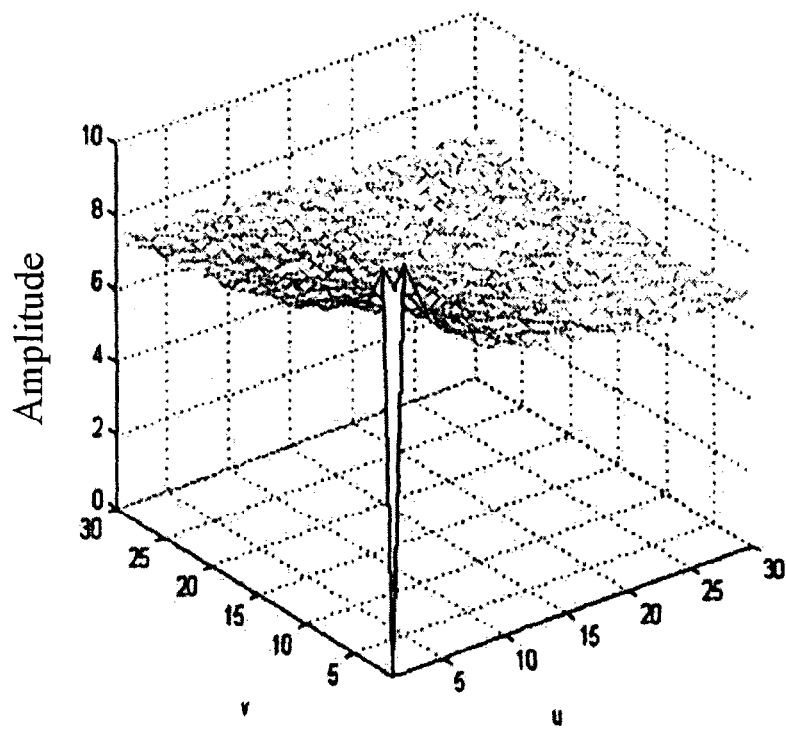
FIG. 9 depicts average vector components obtained by averaging a plurality of DCTed ultrasound image signals representative of a predetermined organ.
Figure 10:
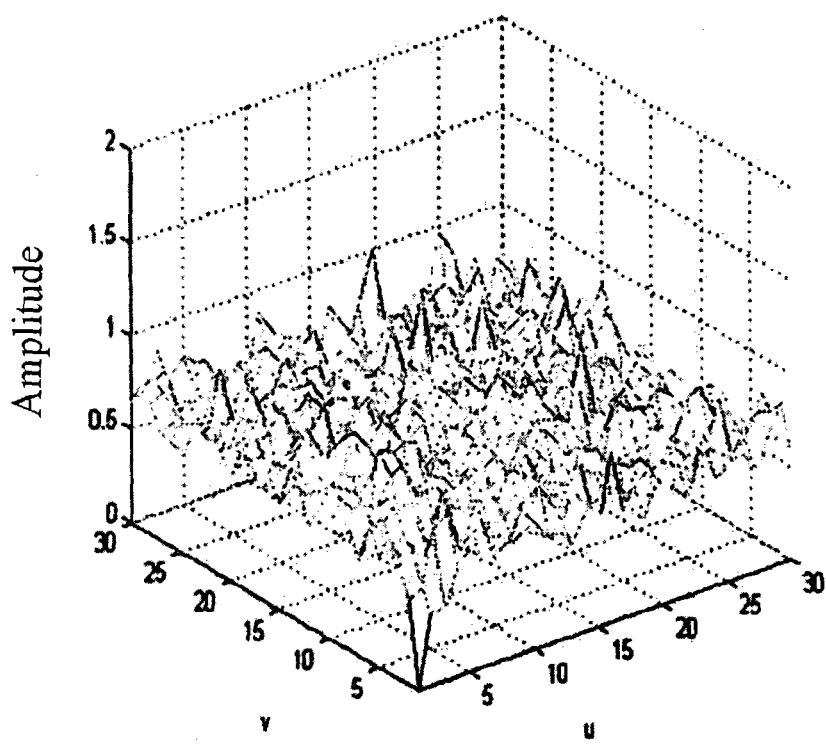
FIG. 10 depicts standard deviation vector components of DCTed ultrasound image signals representative of a predetermined organ.

FIGS. 9 and 10 illustrate the components corresponding to upper left region 84 in FIG. 8B of the average vector and the standard deviation vector, which was obtained by using Equations 4 and 5 respectively, for the ultrasound image signal of a predetermined organ.

The average vector $\overline{f}_k$ and the standard deviation vector $\sigma_k$ for the ultrasound image signals classified by the types of organs can be obtained from Equations 6 and 7 with the average vector $\overline{F}_k(u,v)$ and the standard deviation vector $\sigma_k(u,v)$ of the k-th organ, which are obtained by Equations 4 and 5:

$$\overline{f}_k = \{\overline{F}_k(0,0), \overline{F}_k(0,1), \ldots, \overline{F}_k(U,V)\}, k=1, 2, \ldots, K \qquad \text{Eq. 6}$$

$$\sigma_k = \{\sigma_k(0,0), \sigma_k(0,1), \ldots, \sigma_k(U,V)\}, k=1, 2, \ldots, K \qquad \text{Eq. 7}$$

The average vector and the standard deviation vector for the ultrasound image signals classified by the types of organs are provided to controller 9.

Controller 9 selects the optimal organ image signal for the inputted ultrasound signal from the ultrasound image signals classified by the types of organs in database 5 and displays it with information on the name of the organ using the feature vector f for the inputted ultrasound image signal and the average vector $\overline{f}_k$ and the standard deviation vector $\sigma_k$ for the ultrasound image signals classified by the types of organs. More particularly, the distances between the inputted ultrasound image signal and the ultrasound image signals classified by the types of organs in database 5 are computed in order to select the optimal organ image signal. In a preferred embodiment of the present invention, the distances between the inputted ultrasound image signal and the ultrasound image signals classified by the types of organs in database 5 are calculated as a Mahalanobis distance:

$$d(f, \overline{f}_k) = \left\| \frac{f - \overline{f}_k}{\sigma_k} \right\|, k = 1, 2, \ldots, K \qquad \text{Eq. 8}$$

After calculating all the distances between the inputted ultrasound image signal and the ultrasound image signals classified by the types of organs in database 5 using the Mahalanobis distance, controller 9 determines the ultrasound image signal classified by the types of organs corresponding to the shortest distance among the calculated distances as an optimal organ image signal for the inputted ultrasound image signal.

According to the present invention, the parameters do not need to be manually operated to recognize an organ since the organ can be accurately recognized by using the feature vectors of the inputted ultrasound image signal and the ultrasound image signals classified by the types of organs in database.

Although the present invention has been shown and described with respect to particular embodiments, those skilled in the art will recognize that many changes and modifications may be made without departing from the spirit and scope of the invention as defined in the appended claims.

What is claimed is:

1. An apparatus for identifying human organs from an input ultrasound image signal, comprising:
   a first feature vector determiner for determining a first feature vector of the input ultrasound image signal;
   a memory for storing a list of predetermined types of organs and a plurality of ultrasound images in association with each of the predetermined types of organs;
   a second feature vector determiner for determining respective second feature vectors of the ultrasound images for each of the predetermined types of organs;
   a calculator for calculating an average vector and a standard deviation vector of the second feature vectors for each of the predetermined types of organs; and
   an organ determiner for selecting one of the average vectors for the predetermined types of organs based on the first feature vector and the average vectors and the standard deviation vectors for the predetermined types of organs, and for determining an organ corresponding to the selected average vector as an organ corresponding to the input ultrasound image signal.

2. The apparatus of claim 1, wherein the first feature vector determiner comprises a first pre-processor and a first feature vector extractor,
   wherein the first pre-processor includes a first sub-sampler for sub-sampling the input ultrasound image signal; a first window-processor for window-processing the sub-sampled ultrasound image signal; and a first normalizer for normalizing brightness and contrast of the window-processed ultrasound image signal, and
   wherein the first feature vector extractor includes a first log power spectrum extractor for extracting a first log power spectrum from the pre-processed ultrasound image signal; and a first feature vector detector for detecting the first feature vector from the first log power spectrum.

3. The apparatus of claim 2, wherein the second feature vector determiner comprises a second pre-processor and a second feature vector extractor,
   wherein the second pre-processor includes a second sub-sampler for sub-sampling the ultrasound images stored in the memory; a second window-processor for window-processing the sub-sampled ultrasound images; and a second normalizer for normalizing brightness and contrast of the normalized ultrasound images, and
   wherein said second feature vector extractor includes a second log power spectrum extractor for extracting second log power spectrums from the pre-processed ultrasound images; and a second feature vector detector for detecting the second feature vectors from the second log power spectrums of the pre-processed ultrasound images.

4. The apparatus of claim 3, wherein the organ determiner comprises:
   a calculator for calculating distances between the first feature vector and the average vectors for the predetermined types of organs; and
   a determiner for determining an organ corresponding to an average vector having the shortest distance from the first feature vector as the organ corresponding to the input ultrasound image signal.

5. The apparatus of claim 4, wherein the first log power spectrum $F(u,v)$ is computed by the following equation:

$$F(u,v)=\log|\Im\{I_N(m,n)\}|$$

where $(m,n)$ represents a coordinate position of an organ in the input ultrasound image, $I_N(m,n)$ is the first normalized input ultrasound image signal, and $\Im$ is a Discrete Fourier Transform operator; and wherein the first feature vector f of the input ultrasound image signal is represented by the following equation:

$$f=\{F(0,0), F(0,1), \ldots, F(U,V)\}$$

where U and V are integers for delimiting a predetermined frequency region to determine the first feature vector of the input ultrasound image signal.

6. The apparatus of claim 4, wherein the average vector $\overline{F}_k(u,v)$ of the ultrasound images for the k-th organ is calculated by the following equation:

$$\overline{F}_k(u,v) = \frac{1}{M}\sum_{i=1}^{M} F_k^i(u,v), k = 1, 2, \ldots, K$$

where $F^i_k(u,v)$ is the second feature vector of the i-th ultrasound image for the k-th organ, M is the number of the ultrasound images for the k-th organ, and K is the number of the types of organs stored in the memory.

7. The apparatus of claim 4, wherein the standard deviation vector $\sigma_k(u,v)$ of the ultrasound images for the k-th organ is calculated by the following equation:

$$\sigma_k(u,v) = \left\{\frac{1}{M}\sum_{i=1}^{M} \{F_k^i(u,v) - \overline{F}_k(u,v)\}^2\right\}^{\frac{1}{2}} \quad k = 1, 2, \ldots, K$$

where $F^i_k(u,v)$ is the second feature vector of the i-th ultrasound image for the k-th organ, $\overline{F}_k(u,v)$ is the average vector of the ultrasound images for the k-th organ, M is the number of the ultrasound images for the k-th organ, and K is the number of the types of organs stored in the memory.

8. The apparatus of claim 4, wherein the distance between the first feature vector and the average vectors for the predetermined types of organs is computed according to the following equation, $$d(f, \overline{f}_k) = \left\|\frac{f - \overline{f}_k}{\sigma_k}\right\|, k = 1, 2, \ldots, K$$

where f is the first feature vector, $\overline{f}_k$ is the average vector of the ultrasound images for the k-th organ, and $\sigma_k$ is the standard deviation vector of the ultrasound images for the k-th organ.

9. A method for identifying human organs from an input ultrasound image signal comprising the steps of:
   determining a first feature vector of the input ultrasound image signal;
   storing in a memory a list of predetermined types of organs and a plurality of ultrasound images in association with each of the predetermined types of organs;
   determining respective second feature vectors of the ultrasound images for each of the predetermined types of organs;
   calculating an average vector and a standard deviation vector of the second feature vectors for each of the predetermined types of organs;
   selecting one of the average vectors based on the first feature vector and the average vectors and the standard deviation vectors for the predetermined types of organs; and determining an organ corresponding to the selected average vector as the organ corresponding to the input ultrasound image signal.

10. The method of claim 9, wherein the first feature vector determining step comprises a first pre-processing step and a first feature vector extracting step, wherein the first pre-processing step includes the steps of sub-sampling the input ultrasound image signal; window-processing the sub-sampled ultrasound image signal; and normalizing brightness and contrast of the window-processed ultrasound image signal, and wherein the first feature vector extracting step includes the steps of extracting a first log power spectrum from the pre-processed ultrasound image signal; and detecting the first feature vector from the first log power spectrum.

11. The method of claim 10, wherein the second feature vector determining step comprises a second pre-processing step and a second feature vector extracting step, wherein the second pre-processing step includes the steps of sub-sampling the ultrasound images stored in the memory; window-processing the sub-sampled ultrasound images; and normalizing brightness and contrast of the window-processed ultrasound images, and wherein the second feature vector extracting step includes the steps of extracting second log power spectrums from the pre-processed ultrasound images; and detecting the second feature vectors from the second log power spectrums.

12. The method of claim 11, wherein the organ determining step comprises the steps of calculating distances between the first feature vector and the average vectors for the predetermined types of organs; and determining an organ corresponding to an average vector having the shortest distance from the first feature vector as the organ corresponding to the input ultrasound image signal.

13. The method of claim 12, wherein the first log power spectrum F(u,v) is computed by the following equation:

$$F(u,v) = \log|\Im\{I_N(m,n)\}|$$

where (m,n) is a coordinate position of an organ in the input ultrasound image, $I_N(m,n)$ is the first normalized input ultrasound image signal, and $\Im$ is a Discrete Fourier Transform operator, and wherein the first feature vector f of the input ultrasound image signal is represented by the following equation:

$$f = \{F(0.0), F(0.1), \ldots, F(U,V)\}$$

where U and V are integers for delimiting a predetermined frequency region to determine the first feature vector of the input ultrasound image signal.

14. The method of claim 12, wherein the average vector $\overline{F}_k(u,v)$ of the ultrasound images for the k-th organ is calculated by the following equation:

$$\overline{F}_k(u,v) = \frac{1}{M}\sum_{i=1}^{M} F_k^i(u,v), k = 1, 2, \ldots, K$$

where $F_k^i(u,v)$ is the second feature vector of the i-th ultrasound image for the k-th organ, M is the number of the ultrasound images for the k-th organ, and K is the number of the types of organs stored in the memory.

15. The method of claim 12, wherein the standard deviation vector $\sigma_k(u,v)$ of the ultrasound images for the k-th organ is calculated by the following equation:

$$\sigma_k(u,v) = \left\{\frac{1}{M}\sum_{i=1}^{M}\{F_k^i(u,v) - \overline{F}_k(u,v)\}^2\right\}^{\frac{1}{2}} \quad k = 1, 2, \ldots, K$$

where $F_k^i(u,v)$ is the second feature vector of the i-th ultrasound image for the k-th organ, $\overline{F}_k(u,v)$ is the average vector of the ultrasound images for the k-th organ, M is the number of the ultrasound images for the k-th organ, and K is the number of the types of organs stored in the memory.

16. The method of claim 12, wherein the distance between the first feature vector and the average vectors for the predetermined types of organs is computed according to the following equation, $$d(f, \overline{f}_k) = \left\|\frac{f - \overline{f}_k}{\sigma_k}\right\|, k = 1, 2, \ldots, K$$

where f is the first feature vector, $\overline{f}_k$ is the average vector of the ultrasound images for the k-th organ, and $\sigma_k$ is the standard deviation vector of the ultrasound images for the k-th organ.

* * * * *